United States Patent
Zuo et al.

(10) Patent No.: US 10,605,797 B2
(45) Date of Patent: Mar. 31, 2020

(54) FLUID ANALYSIS METHODS AND APPARATUS FOR DETERMINING GAS-OIL RATIO

(71) Applicant: Schlumberger Technology Corporation, Sugar Land, TX (US)

(72) Inventors: Youxiang Zuo, Burnaby (CA); Vinay K. Mishra, Katy, TX (US); Oliver C. Mullins, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 400 days.

(21) Appl. No.: 14/620,659

(22) Filed: Feb. 12, 2015

(65) Prior Publication Data
US 2015/0226063 A1  Aug. 13, 2015

Related U.S. Application Data (60) Provisional application No. 61/938,797, filed on Feb. 12, 2014.

(51) Int. Cl.
*E21B 49/08* (2006.01)
*G01N 33/28* (2006.01)

(52) U.S. Cl.
CPC ......... *G01N 33/2841* (2013.01); *E21B 49/08* (2013.01); *E21B 2049/085* (2013.01)

(58) Field of Classification Search
None
See application file for complete search history.

(56) References Cited

U.S. PATENT DOCUMENTS

| | | | |
|---|---|---|---|
| 6,274,865 B1 * | 8/2001 | Schroer ................ | E21B 47/102 250/255 |
| 7,920,970 B2 | 4/2011 | Zuo et al. | |
| 7,966,273 B2 | 6/2011 | Hegeman et al. | |
| 2004/0193375 A1 * | 9/2004 | Dong ..................... | E21B 47/10 702/13 |
| 2005/0119911 A1 * | 6/2005 | Ayan ..................... | G01V 11/00 703/10 |
| 2007/0137292 A1 * | 6/2007 | Xian ................... | G01N 33/2823 73/152.18 |
| 2008/0141767 A1 * | 6/2008 | Raghuraman ...... | G01N 33/2823 73/152.55 |
| 2009/0032249 A1 * | 2/2009 | Morales ................ | E21B 43/34 166/250.01 |
| 2009/0192768 A1 * | 7/2009 | Zuo .................... | G01N 33/2823 703/2 |
| 2009/0235731 A1 * | 9/2009 | Zuo .................... | G01N 33/2823 73/152.28 |
| 2009/0288881 A1 * | 11/2009 | Mullins .................. | E21B 7/04 175/50 |

(Continued)

*Primary Examiner* — Khaja Ahmad
(74) *Attorney, Agent, or Firm* — Trevor G. Grove (57) ABSTRACT

The present disclosure relates to methods and apparatus for determining a gas-oil ratio based on downhole fluid analysis measurements and calibrated gas-oil ratio parameters. According to certain embodiments, the parameters for calculating the gas-oil ratio may be calibrated using historical data from the reservoir. For example, previously determined gas-oil ratios may be employed to calibrate the parameters to the reservoir. The calibrated parameters may then be employed during sampling operations to determine the gas-oil ratio.

20 Claims, 4 Drawing Sheets

(56) References Cited

U.S. PATENT DOCUMENTS

| | | | |
|---|---|---|---|
| 2009/0289628 A1* | 11/2009 | Cao Minh | G01N 24/081 324/303 |
| 2011/0088949 A1* | 4/2011 | Zuo | E21B 49/08 175/48 |
| 2011/0303463 A1* | 12/2011 | Lessi | E21B 21/067 175/50 |
| 2012/0095733 A1* | 4/2012 | Rossi | E21B 43/00 703/2 |
| 2012/0272715 A1 | 11/2012 | Kriel et al. | |

* cited by examiner

FLUID ANALYSIS METHODS AND APPARATUS FOR DETERMINING GAS-OIL RATIO

CROSS-REFERENCE TO RELATED APPLICATIONS

This application claims benefit of U.S. Provisional Patent Application Ser. No. 61/938,797, filed Feb. 12, 2014, which is herein incorporated by reference.

BACKGROUND OF THE DISCLOSURE

Wellbores (also known as boreholes) are drilled to penetrate subterranean formations for hydrocarbon prospecting and production. During drilling operations, evaluations may be performed of the subterranean formation for various purposes, such as to locate hydrocarbon-bearing formations and manage the production of hydrocarbons from these formations. To conduct formation evaluations, the drill string may include one or more drilling tools that test and/or sample the surrounding formation, or the drill string may be removed from the wellbore, and a wireline tool may be deployed into the wellbore to test and/or sample the formation. These drilling tools and wireline tools, as well as other wellbore tools conveyed on coiled tubing, drill pipe, casing or other conveyers, are also referred to herein as "downhole tools."

Formation evaluation may involve drawing fluid from the formation into a downhole tool for testing and/or sampling. Various devices, such as probes and/or packers, may be extended from the downhole tool to isolate a region of the wellbore wall, and thereby establish fluid communication with the subterranean formation surrounding the wellbore. Fluid may then be drawn into the downhole tool using the probe and/or packer. Within the downhole tool, the fluid may be directed to one or more fluid analyzers and sensors that may be employed to detect properties of the fluid. The properties of the fluid may be employed to determine reservoir architecture, connectivity, and compositional gradients, among others.

SUMMARY

The present disclosure relates to a downhole fluid analysis method that includes withdrawing formation fluid into a downhole tool disposed within a wellbore extending into a reservoir and analyzing the formation fluid within the downhole tool to determine concentrations of carbon components in the formation fluid. The method further includes calculating a gas-oil ratio based on the determined concentrations and calibrated gas-oil ratio parameters determined from analysis of a previous formation fluid sample obtained from the reservoir.

The present disclosure also relates to a downhole tool that includes a fluid analyzer to determine concentrations of carbon components in formation fluid sampled from a reservoir. The downhole tool also includes a controller designed to execute instructions stored within the downhole tool to calculate a gas-oil ratio based on the determined concentrations and calibrated gas-oil ratio parameters determined from analysis of a previous formation fluid sample obtained from the reservoir.

The present disclosure further relates to a downhole fluid analysis method that includes withdrawing formation fluid into a downhole tool disposed within a wellbore extending into a reservoir and analyzing the formation fluid within the downhole tool to determine properties of the formation fluid. The method also includes calculating calibrated gas-oil ratio parameters based on historical gas-oil ratio data for the reservoir and calculating a gas-oil ratio for the formation fluid based on the determined properties and the calibrated gas-oil ratio parameters.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the present disclosure provides many different embodiments, or examples, for implementing different features of various embodiments. Specific examples of components and arrangements are described below to simplify the present disclosure. These are, of course, merely examples and are not intended to be limiting.

The present disclosure relates to methods for determining a gas-oil ratio based on downhole fluid analysis measurements and calibrated gas-oil ratio parameters. According to certain embodiments, parameters for calculating the gas-oil ratio may be calibrated using historical data from the reservoir. For example, previously determined gas-oil ratios and/or composition data from a previous formation fluid sample may be employed to calibrate the parameters to the reservoir. The calibrated parameters may then be employed during sampling operations to determine the gas-oil ratio in substantially real time.

Figure 1:
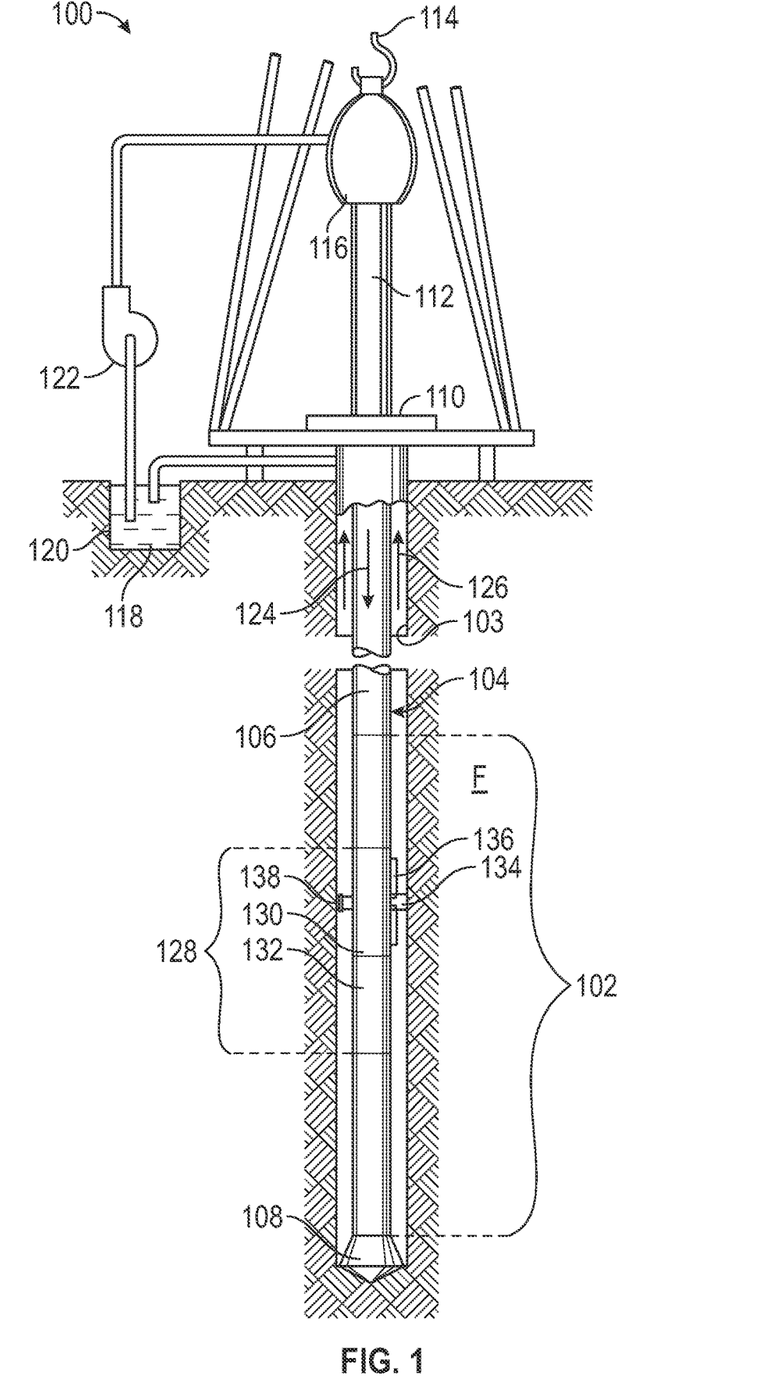
FIG. 1 is a schematic view of an embodiment of a wellsite system that may employ downhole fluid analysis methods for determining a gas-oil ratio, according to aspects of the present disclosure.
Figure 2:
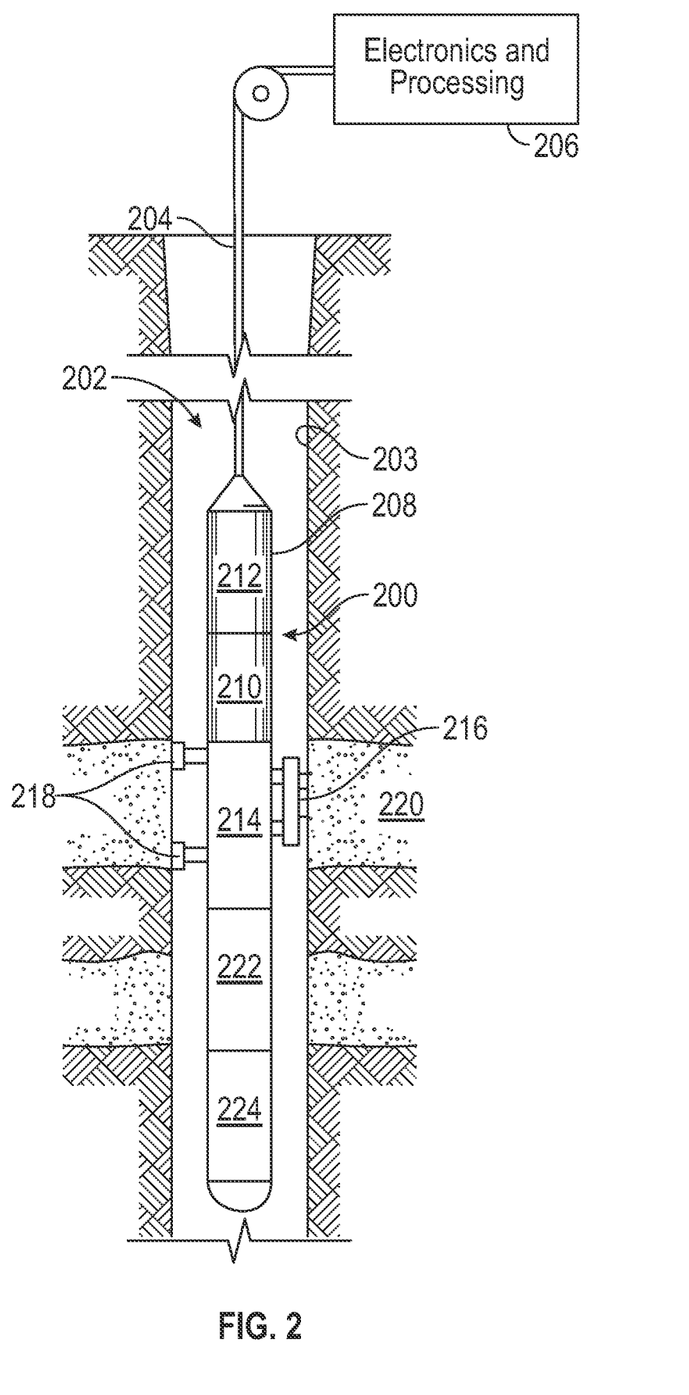
FIG. 2 is a schematic view of another embodiment of a wellsite system that may employ downhole fluid analysis methods for determining a gas-oil ratio, according to aspects of the present disclosure.

FIGS. 1 and 2 depict examples of wellsite systems that may employ the fluid analysis systems and techniques described herein. FIG. 1 depicts a rig 100 with a downhole tool 102 suspended therefrom and into a wellbore 104 via a drill string 106. The downhole tool 100 has a drill bit 108 at its lower end thereof that is used to advance the downhole tool into the formation and form the wellbore. The drillstring 106 is rotated by a rotary table 110, energized by means not shown, which engages a kelly joint 112 at the upper end of the drillstring 106. The drillstring 106 is suspended from a hook 114, attached to a traveling block (also not shown), through the kelly joint 112 and a rotary swivel 116 that permits rotation of the drillstring 106 relative to the hook 114. The rig 100 is depicted as a land-based platform and derrick assembly used to form the wellbore 104 by rotary drilling. However, in other embodiments, the rig 100 may be an offshore platform.

Drilling fluid or mud 118 is stored in a pit 120 formed at the well site. A pump 122 delivers the drilling fluid 118 to the interior of the drillstring 106 via a port in the swivel 116, inducing the drilling fluid to flow downwardly through the drillstring 106 as indicated by a directional arrow 124. The drilling fluid exits the drillstring 106 via ports in the drill bit 108, and then circulates upwardly through the region between the outside of the drillstring and the wall of the wellbore, called the annulus, as indicated by directional arrows 126. The drilling fluid lubricates the drill bit 108 and carries formation cuttings up to the surface as it is returned to the pit 120 for recirculation.

The downhole tool 102, sometimes referred to as a bottom hole assembly ("BHA"), may be positioned near the drill bit 108 and includes various components with capabilities, such as measuring, processing, and storing information, as well as communicating with the surface. A telemetry device (not shown) also may be provided for communicating with a surface unit (not shown).

The downhole tool 102 further includes a sampling system 128 including a fluid communication module 130 and a sampling module 132. The modules may be housed in a drill collar for performing various formation evaluation functions, such as pressure testing and sampling, among others. As shown in FIG. 1, the fluid communication module 130 is positioned adjacent the sampling module 132; however the position of the fluid communication module 130, as well as other modules, may vary in other embodiments. Additional devices, such as pumps, gauges, sensor, monitors or other devices usable in downhole sampling and/or testing also may be provided. The additional devices may be incorporated into modules 130 and 132 or disposed within separate modules included within the sampling system 128.

The fluid communication module 130 includes a probe 134, which may be positioned in a stabilizer blade or rib 136. The probe 134 includes one or more inlets for receiving formation fluid and one or more flowlines (not shown) extending into the downhole tool for passing fluids through the tool. In certain embodiments, the probe 134 may include a single inlet designed to direct formation fluid into a flowline within the downhole tool. Further, in other embodiments, the probe may include multiple inlets that may, for example, be used for focused sampling. In these embodiments, the probe may be connected to a sampling flow line, as well as to guard flow lines. The probe 134 may be movable between extended and retracted positions for selectively engaging a wall 103 of the wellbore 104 and acquiring fluid samples from the formation F. One or more setting pistons 138 may be provided to assist in positioning the fluid communication device against the wellbore wall.

FIG. 2 depicts an example of a wireline downhole tool 200 that may employ the systems and techniques described herein. The downhole tool 200 is suspended in a wellbore 202 from the lower end of a multi-conductor cable 204 that is spooled on a winch at the surface. The cable 204 is communicatively coupled to an electronics and processing system 206. The downhole tool 200 includes an elongated body 208 that houses modules 210, 212, 214, 222, and 224, that provide various functionalities including fluid sampling, fluid testing, operational control, and communication, among others. For example, the modules 210 and 212 may provide additional functionality such as fluid analysis, resistivity measurements, operational control, communications, coring, and/or imaging, among others.

As shown in FIG. 2, the module 214 is a fluid communication module 214 that has a selectively extendable probe 216 and backup pistons 218 that are arranged on opposite sides of the elongated body 208. The extendable probe 216 is configured to selectively seal off or isolate selected portions of the wall 203 of the wellbore 202 to fluidly couple to the adjacent formation 220 and/or to draw fluid samples from the formation 220. The probe 216 may include a single inlet or multiple inlets designed for guarded or focused sampling. The formation fluid may be expelled to the wellbore through a port in the body 208 or the formation fluid may be sent to one or more fluid sampling modules 222 and 224. The fluid sampling modules 222 and 224 may include sample chambers that store the formation fluid. In the illustrated example, the electronics and processing system 206 and/or a downhole control system are configured to control the extendable probe assembly 216 and/or the drawing of a fluid sample from the formation 220.

Figure 3:
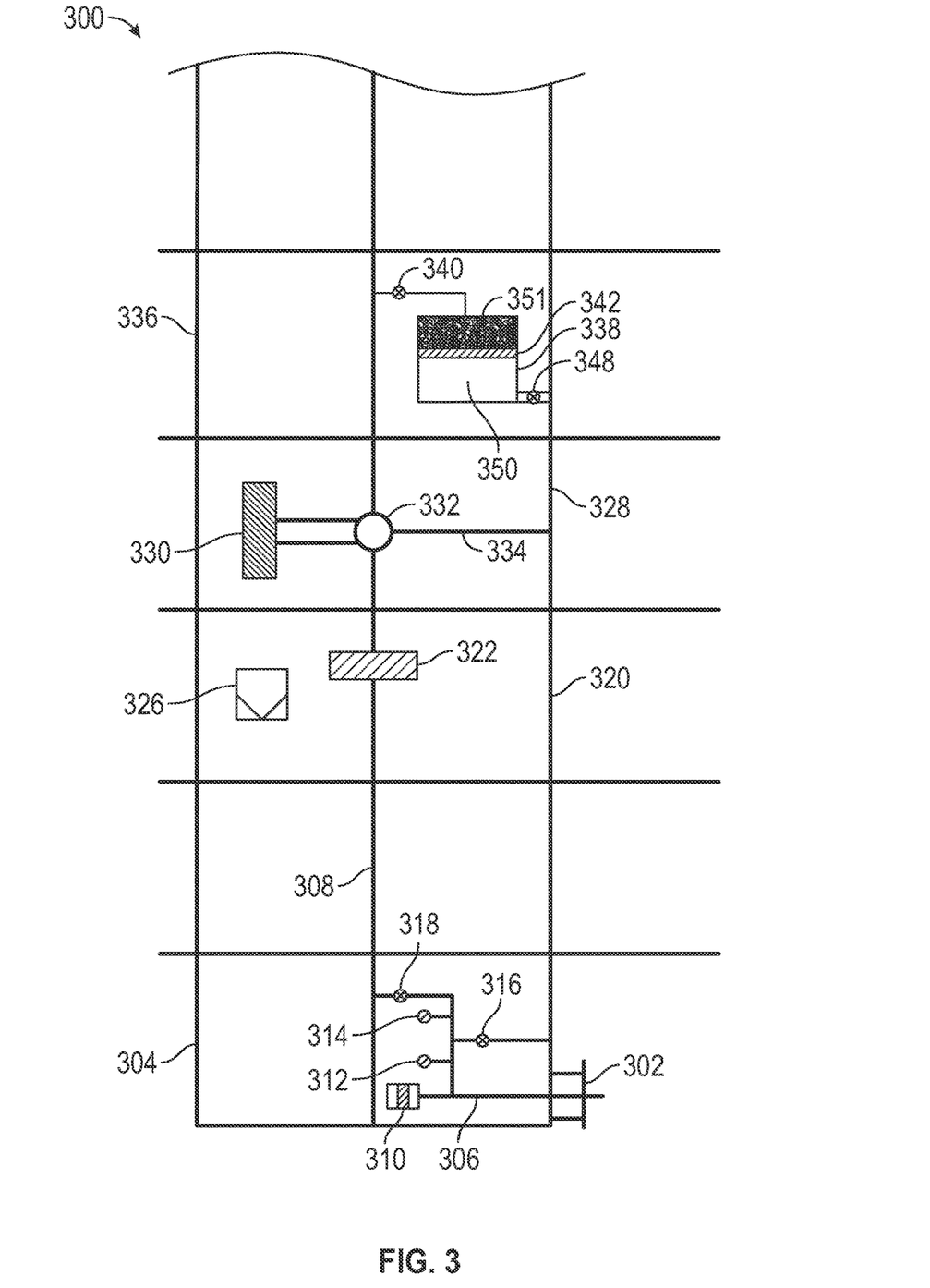
FIG. 3 is a schematic representation of an embodiment of a downhole tool that may employ downhole fluid analysis methods for determining a gas-oil ratio, according to aspects of the present disclosure.

FIG. 3 is a schematic diagram of a portion of a downhole tool 300 that may employ the fluid analysis methods described herein. For example, the downhole tool 300 may be a drilling tool, such as the downhole tool 102 described above with respect to FIG. 1. Further, the downhole tool 300 may be a wireline tool, such as the downhole tool 200 described above with respect to FIG. 2. Further, in other embodiments, the downhole tool may be conveyed on wired drill pipe, a combination of wired drill pipe and wireline, or other suitable types of conveyance.

As shown in FIG. 3, the downhole tool 300 includes a fluid communication module 304 that has a probe 302 for directing formation fluid into the downhole tool 300. According, to certain embodiments, the fluid communication module 304 may be similar to the fluid communication modules 130 and 214, described above with respect to FIGS. 1 and 2, respectively. As shown in FIGS. 1-3, the probe includes an extendable probe that moves out from the body of the downhole tool to engage the formation. However, in other embodiments, the probe may include an expandable packer with a drain that engages the formation to draw formation fluid into the downhole tool. Further, in other embodiments, two or more inflatable packers may be disposed on opposite sides of an inlet in the body of the downhole tool that draws formation fluid into the downhole tool. Moreover, more than one probe may be employed to draw formation fluid into the downhole tool.

The fluid communication module 304 includes a probe flowline 306 that directs the fluid to a primary flowline 308 that extends through the downhole tool 300. The fluid communication module 304 also includes a pump 310 and pressure gauges 312 and 314 that may be employed to conduct formation pressure tests. An equalization valve 316 may be opened to expose the flowline 306 to the pressure in the wellbore, which in turn may equalize the pressure within the downhole tool 300. Further, an isolation valve 318 may be closed to isolate the formation fluid within the flowline 306, and may be opened to direct the formation fluid from the probe flowline 306 to the primary flowline 308.

The primary flowline 308 directs the formation fluid through the downhole tool to a fluid analysis module 320 that includes a fluid analyzer 322 that can be employed to provide downhole fluid analysis (DFA) measurements. For example, the fluid analyzer 322 may include an optical spectrometer and/or a gas analyzer designed to measure properties such as, optical density, fluid fluorescence, fluid composition, and the fluid gas oil ratio (GOR), among others. One or more additional measurement devices, such as temperature sensors, pressure sensors, viscosity sensors, density sensors, resistivity sensors, chemical sensors (e.g., for measuring pH or $H_2S$ levels), and gas chromatographs, also may be included within the fluid analyzer 322. In certain embodiments, the fluid analyzer 322 measures absorption spectra and translates such measurements into concentrations of several alkane components and groups in the fluid sample. For example, the fluid analyzer 322 may determine the concentrations (e.g., weight percentages) of carbon dioxide ($CO_2$), methane ($CH_4$), ethane ($C_2H_6$), the $C_3$-$C_5$ alkane group, and the lump of hexane and heavier alkane components ($C_{6+}$).

The fluid analysis module 320 also may include a controller 326, such as a microprocessor or control circuitry, designed to calculate certain fluid properties based on the sensor measurements. For example, the controller 326 may calculate the GOR, as described further below with respect to FIG. 4. Further, in certain embodiments, the controller 326 may govern sampling operations based on the fluid measurements or properties. Moreover, in other embodiments, the controller 326 may be disposed within another module of the downhole tool 300.

The downhole tool 300 also includes a pump out module 328 that has a pump 330 designed to provide motive force to direct the fluid through the downhole tool 300. According to certain embodiments, the pump 330 may be a hydraulic displacement unit that receives fluid into alternating pump chambers. A valve block 332 may direct the fluid into and out of the alternating pump chambers. The valve block 332 also may direct the fluid exiting the pump 330 through the remainder of the primary flowline 308 (e.g., towards the sample module 336) or may divert the fluid to the wellbore through an exit flowline 334.

The downhole tool 300 also includes one or more sample modules 336 designed to store samples of the formation fluid within a sample chamber 338. As shown in FIG. 3, a single sample chamber 338 is included within the sample module 336. However, in other embodiments, multiple sample chambers may be included within the sample module 336 to provide for storage of multiple formation fluid samples. Further, in other embodiments, multiple sample modules 336 may be included within the downhole tool. Moreover, other types of sample chambers, such as single phase sample bottles, among others, may be employed in the sample module 336.

The sample module 336 includes a valve 340 that may be actuated to divert the formation fluid into the sample chamber 338. The sample chamber 338 includes a floating piston 342 that divides the sample chamber into two volumes 350 and 351. As the formation fluid flows through the primary flowline 308, the valve 340 may be actuated to divert the formation fluid into the volume 350. In certain embodiments, the pump 330 may provide the motive force to direct the fluid through the primary flowline 308 and into the sample chamber 338. The formation fluid may be stored within the volume 351 and, in certain embodiments, may be brought to the surface for further analysis. The sample module 336 also may include a valve 348 that can be opened to expose the volume 350 of the sample chamber 338 to the annular pressure. In certain embodiments, the valve 348 may be opened to allow buffer fluid to exit the volume 350 to the wellbore, which may provide backpressure during filling of the volume 351 that receives formation fluid. In other embodiments, the volume 350 may be filled with a low pressure gas that provides backpressure during filling of the volume 351.

Figure 4:
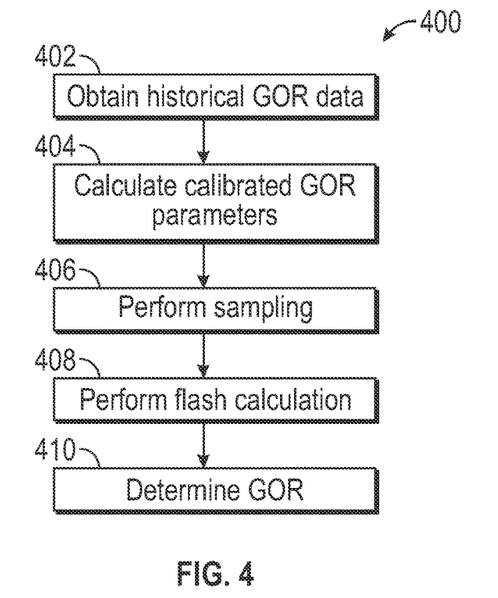
FIG. 4 is a flowchart depicting a fluid analysis method for determining a gas-oil ratio, according to aspects of the present disclosure.

FIG. 4 is a flowchart depicting an embodiment of a method 400 that may be employed to determine the GOR of formation fluid based on DFA measurements. According to certain embodiments, the method 400 may be executed, in whole or in part, by the controller 326 (FIG. 3). For example, the controller 326 may execute code stored within circuitry of the controller 326, or within a separate memory or other tangible readable medium, to perform the method 400. In certain embodiments, the method 400 may be wholly or partially executed while the tool 300 is disposed within a wellbore, allowing a substantially real-time determination of the GOR of the formation fluid. Further, in certain embodiments, the controller 326 may operate in conjunction with a surface controller, such as the electronics and processing system 206 (FIG. 2), which may perform one or more operations of the method 400.

As discussed further below, the method 400 provides techniques for calculating the GOR of formation fluid by simulating a flash evaporation process for the formation fluid from downhole conditions to standard conditions (e.g., approximately 14.7 psia and 60 degrees F.). The method 400 assumes that the formation fluid exists in a single-phase at downhole conditions. In certain embodiments, the phase may be liquid (e.g., oil) or gas (e.g, gas condensate). Flashing of the formation fluid to standard conditions produces flashed gas and stock tank oil (e.g., flashed liquid). Accordingly, the GOR may be represented by Equation 1 as follows:

$$GOR = \frac{V_g}{V_{sto}} \qquad (1)$$

where $V_g$ is the volume of the flashed gas and $V_{sto}$ is the volume of the STO.

Assuming that gas as at standard conditions follows the ideal gas law, the volume of the flashed gas may be represented by Equation 2 as follows:

$$V_g = \frac{n_g R T_{std}}{P_{std}} = 23.69 n_g \qquad (2)$$

where $n_g$ is the mole ratio of the flashed gas in the formation fluid at standard conditions; R is the universal gas constant; $T_{std}$ is the temperature at standard conditions (e.g., 60 degrees F.); and $P_{std}$ is the pressure at standard conditions (e.g., 14.7 psia). Further, the volume of the STO may be represented by Equation 3 as follows:

$$V_{sto} = \frac{(1 - n_g) MW_{sto}}{\rho_{sto}} \qquad (3)$$

where $MW_{sto}$ is the molecular weight of the STO; and $\rho_{sto}$ is the density of the STO. As shown above, Equations 2 and 3 include three unknowns, $n_g$, $MW_{sto}$, and $\rho_{sto}$, which can be determined using a combination of historical GOR data and downhole fluid analysis data, as described below with respect to the method 400.

The method 400 may begin by obtaining (block 402) historical GOR data for the reservoir. For example, the historical GOR data may include formation fluid properties, such as fluid composition, GOR, and API gravity determined from prior analysis of formation fluid existing within the reservoir. According to certain embodiments, the historical GOR data may represent the results of laboratory analysis, such as pressure-volume-temperature (PVT) analysis, performed on formation fluid samples retrieved from the wellbore. The historical GOR data also may represent previous downhole fluid analysis (DFA) results. Further, in certain embodiments, the historical GOR data may be retrieved from a database, such as a PVT (pressure-volume-temperature) database. The PVT database may store the weight percentage, molecular weight, molar percentage, and specific gravity of single carbon number alkane components, as well as PVT properties (e.g., GOR, API gravities, formation volume factor (FVF), densities, and viscosities) for a large number of samples from different petroleum reservoirs throughout the world.

The historical GOR data may then be employed to calculate (block 404) calibrated parameters for determining the GOR. For example, an API gravity previously determined for the reservoir may be employed to determine the density, and therefore the specific gravity, of the STO as follows:

$$\rho_{sto} = SG_{sto} = \frac{141.5}{API + 131.5} \tag{4}$$

where API represents the API gravity and $SG_{sto}$ is the specific gravity of the STO. The molecular weight of the lump of hexane and heavier alkane components ($C_{6+}$) also may be estimated using the specific gravity of the STO from Equation 4 as follows:

$$MW_{C6+} = \exp\left(\frac{SG_{sto} - 0.172}{0.12415}\right) \tag{5}$$

where $MW_{C6+}$ represents the molecular weight of the lump of hexane and heavier alkane components.

The values 141.5 and 131.5 in Equation 4 are fixed constants to convert API gravity to specific gravity. The values of 0.172 and 0.12415 in Equation 5 represent constants that have been shown to apply to many reservoirs based on an analysis of PVT data and/or prior DFA data; however, in other embodiments, the values of these constants in Equation 5 may vary. For example, in certain embodiments, the values of these constants may be adjusted based on additional analysis results. For example, the measured specific gravities of formation fluid samples may be compared to the calculated molecular weights for the group of $C_{6+}$ components for these formation fluid samples to adjust the values of the constants in Equation 5. Further, other correlations may be used to obtain the STO density and molecular weight of $C_{6+}$.

The calibrated parameters that may be calculated (block 402) using historical GOR data also include equilibrium constants for carbon components, or groups of carbon components, within the formation fluid. According to certain embodiments, the fluid analyzer 322 may measure the absorption spectra and translate the measurements into the concentrations of individual carbon components and groups of carbon components. For example, the fluid analyzer 322 may determine the weight fractions of carbon dioxide ($CO_2$), methane ($C_1H_4$), ethane ($C_2H_6$), the $C_3$-$C_5$ alkane group including propane, butane, and pentane, and the lump of hexane and heavier alkane components ($C_{6+}$), among others. Accordingly, equilibrium constants ($K_i$) may be determined for the corresponding carbon components including carbon dioxide, the $C_1$ components (e.g., methane), the $C_2$ components (e.g., ethane), the $C_3$-$C_5$ components, and the $C_{6+}$ components.

The equilibrium constant ($K_i$) represents the ratio of the vapor mole fraction of a given component, or group of components, ($y_i$) to the liquid mole fraction ($x_i$) of the given component, or group of components. At standard conditions, the equilibrium constants for the carbon dioxide, $C_1$, $C_2$, and $C_3$-$C_5$ components may be calculated according to the Wilson equation as shown in Equation 6:

$$K_i = \frac{y_i}{x_i} = \frac{P_{ci}}{P_{std}} \exp\left[5.373(1 + \omega_i)\left(1 - \frac{T_{ci}}{T_{std}}\right)\right] \tag{6}$$

where $P_{ci}$, $T_{ci}$ and $\omega_i$ are the critical pressure, critical temperature and acentric factor, respectively, for the given component, or group of components. The equilibrium constants for the carbon dioxide, $C_1$, and $C_2$ components can be directly calculated by employing the physical properties shown in Table 1 in Equation 6.

TABLE 1

Component physical properties:

| Component (units) | MW (g/mol) | $P_c$ (atm) | $T_c$ (K) | $\omega$ |
|---|---|---|---|---|
| $CO_2$ | 44.01 | 72.85 | 304.20 | 0.2276 |
| $C_1$ | 16.04 | 45.39 | 190.60 | 0.0115 |
| $C_2$ | 30.07 | 48.08 | 305.30 | 0.0995 |
| $C_3$ | 44.10 | 41.93 | 369.80 | 0.1523 |
| i-$C_4$ | 58.12 | 36.00 | 408.10 | 0.1770 |
| n-$C_4$ | 58.12 | 37.46 | 425.10 | 0.2002 |
| i-$C_5$ | 72.15 | 33.36 | 460.40 | 0.2279 |
| n-$C_5$ | 72.15 | 33.26 | 469.70 | 0.2515 |

The equilibrium constant for the $C_3$-$C_5$ components can be calculated using the mixed fluid properties, which can be obtained as shown in Equations 7-10:

$$T_{ci} = \frac{\sum_j w_j T_{cj}}{\sum_j w_j} \tag{7}$$

$$P_{ci} = \frac{\sum_j w_j P_{cj}}{\sum_j w_j} \tag{8}$$

$$\omega_i = \frac{\sum_j w_j \omega_j}{\sum_j w_j} \tag{9}$$

$$MW_i = \frac{\sum_j w_j}{\sum_j \frac{w_j}{MW_j}} \tag{10}$$

where $T_{ci}$ is the critical temperature of the mixture of the $C_3$-$C_5$ components; $P_{ci}$ is the critical pressure of the mixture of the $C_3$-$C_5$ components; $\omega_i$ is the acentric factor for the mixture of the $C_3$-$C_5$ components; $MW_i$ is the molecular weight of the mixture of the $C_3$-$C_5$ components; $T_{cj}$ is the critical temperature of the respective $C_3$, $C_4$, and $C_5$ components; $P_{cj}$ is the critical pressure of the respective $C_3$, $C_4$, and $C_5$ components; $\omega_j$ is the acentric factor the respective $C_3$, $C_4$, and $C_5$ components; $MW_j$ is the molecular weight of the respective $C_3$, $C_4$, and $C_5$ components; $w_j$ is the weight fraction of the respective $C_3$, $C_4$, and $C_5$ components within the $C_3$-$C_5$ mixture.

The physical properties ($T_{cj}$, $P_{cj}$, and $\omega_j$) for the $C_3$ and $C_5$ components may be taken directly from Table 1, while the physical properties for the $C_4$ components may be calculated as the average of the i-$C_4$ properties and the n-$C_4$ properties. The molecular weight for the $C_3$-$C_5$ composite concentration may be determined from historical GOR data, such as from DFA measurements, PVT measurements, or the like, performed on formation fluid samples from the reservoir. The weight fractions for the $C_3$ through $C_5$ components (e.g., propane, butane, pentane and their isomers) can then be determined by splitting the molecular weight for the composite concentration into the individual carbon component concentrations using a ratio rule or other empirical correlations known to those skilled in the art. For example, a ratio rule such as a 4:3:2 ratio of $C_3$:$C_4$:$C_5$ can be employed where the $C_3$ through $C_5$ concentration is divided into 4 parts $C_3$ components, 3 parts $C_4$ components, and 2 parts $C_5$ components. However, in other embodiments, other correlations or ratios, may be employed.

As discussed above, Equation 6 may be employed to calculate the equilibrium constants for the carbon dioxide, $C_1$, $C_2$, and $C_3$-$C_5$ components. However, the equilibrium constant for the $C_{6+}$ group of components is determined through additional calculations. In particular, the equilibrium constant $K_{C6+}$ can be determined by conducting a flash calculation at standard conditions. The flash calculation can be developed from the mass balance shown by Equation 11, which applies the definition of $K_i = y_i/x_i$:

$$z_i = n_g y_i + (1-n_g)x_i = n_g K_i x_i + (1-n_g)x_i \quad (11)$$

where $z_i$ is the mole fraction of each respective carbon component, or group of carbon components in 1 mole of formation fluid; $n_g$ is the mole ratio of the flashed gas in the formation fluid at standard conditions; $y_i$ is the mole fraction of each respective component in the flashed gas; $x_i$ is the mole fraction of each respective component in the STO; and $K_i$ is the equilibrium constant for each respective component.

The mole fractions ($z_i$) can be calculated from the weight fractions for each component or group of components. The weight fractions may be determined from historical GOR data, such as from DFA measurements, PVT measurements, or the like, performed on formation fluid samples from the reservoir. For example, the fluid analyzer 321 may measure the absorption spectra and translate the measurements into the weight fractions of carbon dioxide ($CO_2$), methane ($C_1$), ethane ($C_2H_6$), the $C_3$-$C_5$ alkane group including propane, butane, and pentane, and the lump of hexane and heavier alkane components ($C_6+$), among others. In another example, PVT analysis of formation fluid samples drawn from the reservoir may provide the weight fractions for each component, or group of components. The weight fractions can be converted to mole fractions using the following equation:

$$z_i = \frac{w_i/MW_i}{\sum_i (w_i/MW_i)} \quad (12)$$

Rearranging Equation 11 provides the following equations for $x_i$ and $y_i$:

$$x_i = \frac{z_i}{n_g(K_i - 1) + 1} \quad (13)$$

$$y_i = \frac{z_i K_i}{n_g(K_i - 1) + 1} \quad (14)$$

Because the summation of $y_i$ and $x_i$ should be unity, the Rachford-Rice flash equation can be expressed as follows:

$$f(n_g) = \sum_i y_i - \sum_i x_i = \sum_i \frac{z_i(K_i - 1)}{n_g(K_i - 1) + 1} = 0 \quad (15)$$

As discussed above, the equilibrium constants ($K_g$) for the carbon dioxide, $C_1$, $C_2$, and $C_3$-$C_5$ components can be calculated by employing the physical properties, as well as historical GOR composition data for the $C_3$-$C_5$ group, in Equation 6. Further, the mole fractions ($z_i$) can be calculated using the historical GOR composition data in Equation 12 as discussed above.

Equation 15 can then be solved to determine $n_g$. $K_{C6+}$ is adjusted to match historic GOR data. For example, an iterative method, such as the Newton iteration method can be used to solve Equation 15 for $n_g$ at a given $K_{C6+}$. According to certain embodiments, two or more iterative loops may be employed to determine $n_g$ and $K_{C6+}$. An initial guess of $K_{C6+}$ is assumed. Then a first iteration k+1 is performed for Equation 15, for example as shown below in Equation 16:

$$n_g^{k+1} = n_g^k - \frac{f(n_g^k)}{f'(n_g^k)} \quad (16)$$

where $f'(n_g)$ is the derivative of Equation 15. The iteration may continue until Equation 15 is satisfied. In certain embodiments, Equations 1-3 may be employed in the iterative process in conjunction with Equation 15 to solve for the GOR corresponding to the historical GOR data. The value of $K_{C6+}$ may be tuned, for example through iterative adjustment, until the GOR calculated using Equations 1-3 and 15 corresponds to the GOR of the historical data. For example, in certain embodiments, the corresponding GOR may be calculated by performing PVT analysis on a formation fluid sample from the reservoir.

Once Equation 15 has been solved, the resulting value of $K_{C6+}$ may be used as a calibrated GOR parameter, along with the other calibrated GOR parameters, including: the density of the STO ($\rho_{sto}$) determined using Equation 4; the molecular weight ($MW_{C6+}$) of the lump of hexane and heavier alkane components determined using Equation 5; and the other equilibrium constants ($K_i$) determined for the carbon dioxide, $C_1$, $C_2$, and $C_3$-$C_5$ components using Equation 6.

Returning to FIG. 4, the method 400 may then continue by performing (block 406) sampling. For example, as shown in FIG. 3, the downhole tool 300 may be conveyed to a desired location within a wellbore of the same reservoir that corresponds to the calibrated GOR parameters, and the probe 302 may be extended to engage a wall of the wellbore. The pump 330 may be operated to draw formation fluid into the downhole tool 300 through the probe. The formation fluid may then be routed to the fluid analyzer 322 and analyzed as described above with respect to FIG. 3. For example, the fluid analyzer 322 may measure the absorption spectra and translate the measurements into the concentrations of carbon dioxide ($CO_2$), methane ($C_1$), ethane ($C_2H_6$), the $C_3$-$C_5$ alkane group including propane, butane, and pentane, and the lump of hexane and heavier alkane components ($C_{6+}$), among others. In certain embodiments, the controller 326 may operate in conjunction with the fluid analyzer 322 to determine the carbon component concentrations, as well as other formation fluid properties.

A flash calculation may then be performed (block 408) to determine the mole ratio of flashed gas ($n_g$). In particular, the carbon component concentrations determined from the sampling (block 406) may be employed in conjunction with the calibrated GOR parameters to solve Equation 15 for $n_g$. According to certain embodiments, the calibrated GOR parameters (e.g., $MW_{C6+}$, $\rho_{sto}$, and $K_i$) may be retrieved from a memory or other storage of the downhole tool 300. Further, in other embodiments, the calibrated GOR parameters may be transmitted to the controller 326 by a surface processing system, such as the electronics and processing system 206 (FIG. 2). Moreover, the weight fractions of the $C_1$, $C_2$, $C_3$-$C_5$, and $C_{6+}$ components may be converted to mole fractions using Equation 12. The combination of the calibrated GOR parameters and the DFA composition data (e.g., carbon component concentrations) from the current sampling operation can then be input into Equation 15 to solve for the unknown $n_g$.

The GOR for the currently sampled formation fluid can then be determined (block 410) using $n_g$ and Equations 1-3, 13, and 14. As a preliminary matter, $x_i$ and $y_i$ can be calculated for each component, or group of components using Equations 13 and 14. The values of $x_i$ and $y_i$ can then be employed in the following equations to determine the molecular weight of the flashed gas and the STO:

$$MW_g = \sum_i y_i MW_i \quad (17)$$

$$MW_{sto} = \sum_i x_i MW_i \quad (18)$$

where $MW_g$ is the molecular weight of the flashed gas; and $MW_{sto}$ is the molecular weight of the STO. The volume of the flashed gas and the STO can then be calculated using Equations 2 and 3. Finally, the volumes of the flashed gas and the STO can be employed in Equation 1 to calculate the GOR.

Figure 5:
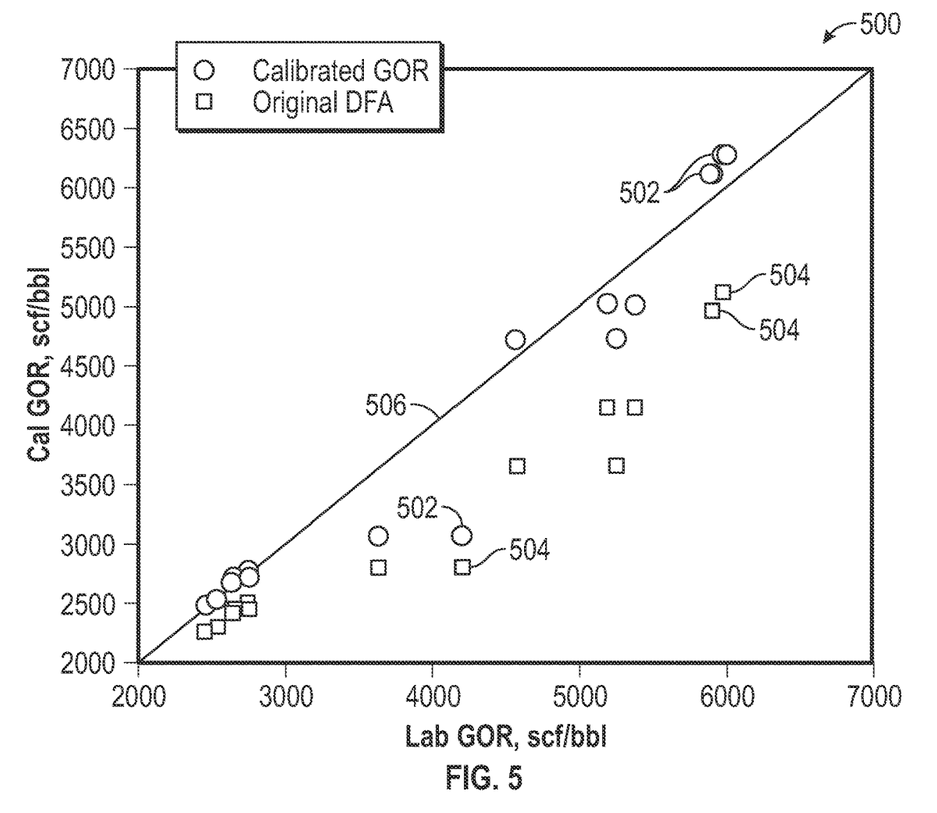
FIG. 5 is a chart depicting an example of gas-oil measurements obtained using the present techniques, according to aspects of the present disclosure.

Calculating the GOR using a combination of historical GOR data and DFA compositional data from a current sampling operation may allow the GOR of sampled formation fluid to be calculated in substantially real-time with results that have been tailored to the properties of the reservoir. FIG. 5 depicts a chart 500 depicting GOR data points 502 and 504 calculated for a sampling operation. The x-axis shows the GOR values calculated during subsequent laboratory analysis, for example, analyzing a sample of formation fluid at the surface using an analysis technique, such as PVT analysis. The y-axis shows the GOR values calculated downhole by the fluid analysis module. The circular data points 502 represent the GOR values that were obtained using the method 400 described herein, while the square data points 504 represent the GOR values that were obtained using DFA methods without calibration of GOR parameters. The line 506 represents direct correspondence between the GOR values obtained through laboratory analysis and the GOR values obtained through DFA, either with calibration or without calibration. As can be seen by comparing data points 502 and 504, the calibrated GOR calculation techniques provide a closer correspondence to the GOR values obtained through laboratory analysis.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A downhole fluid analysis method comprising:
   withdrawing formation fluid, from a wellbore extending into a reservoir comprising the formation fluid, into a sampling system of a downhole sampling tool disposed within the wellbore, wherein the sampling system comprises one or more sensors configured to measure fluid properties of the formation fluid, and wherein the one or more sensors comprises an optical sensor;
   obtaining a density of a stock tank oil by performing a simulated flash of the formation fluid from downhole conditions to standard conditions, wherein the standard conditions are about 14.7 psia and 60 degrees Fahrenheit; and
   analyzing the formation fluid within the downhole sampling tool to determine the fluid properties of the formation fluid using a processor comprising a memory storing instructions configure to:
      determine concentrations of carbon components in the formation fluid within the sample system based on the measured fluid properties, wherein at least one of the measured fluid properties comprises an optical density of the formation fluid as measured by the optical sensor;
      determine one or more calibrated parameters, wherein the one or more calibrated parameters are based at least in part on historical data of a previous formation fluid sample obtained from the reservoir, wherein the one or more calibrated parameters comprise a first equilibrium constant for a flashed carbon component of the previous formation fluid sample, the density of the stock tank oil for the simulated flash of the formation fluid, a second equilibrium constant for a first group of $C_3$-$C_5$ carbon components, a third equilibrium constant for a second group of $C_{6+}$ carbon components, or any combination thereof;
      determine a ratio of one or more of the carbon components based at least in part on the one or more calibrated parameters, wherein the ratio corresponds to one or more flashed carbon components of the formation fluid; and
      calculate a gas-oil ratio of the formation fluid in the sample system based on the concentrations of carbon components and the ratio of the one or more carbon components.

2. The downhole fluid analysis method of claim 1, wherein analyzing comprises measuring an absorption spectra of the formation fluid.

3. The downhole fluid analysis method of claim 1, wherein the processor is configured to calculate the gas-oil ratio based on a flash calculation simulating flashing the formation fluid to standard conditions.

4. The downhole fluid analysis method of claim 1, wherein the ratio is a mole ratio, wherein the processor is configured to solve a flash equation to determine the mole ratio of flashed gas in a simulated flash of the formation fluid, and wherein the mole ratio is used to calculate the gas-oil ratio.

5. The downhole fluid analysis method of claim 1, wherein the one or more calibrated parameters comprise the first equilibrium constant for the flashed carbon component of the previous formation fluid sample.

6. The downhole fluid analysis method of claim 1, wherein the one or more calibrated parameters comprise the third equilibrium constant for the second group of $C_{6+}$ carbon components.

7. The downhole fluid analysis method of claim 1, wherein the one or more calibrated parameters comprise the density of the stock tank oil for the simulated flash of the formation fluid.

8. The downhole fluid analysis method of claim 1, wherein the processor is configured to determine a volume ratio of a volume of flashed gas to a volume of the stock tank oil for the simulated flash of the formation fluid, wherein the volume ratio is used to calculate the gas-oil ratio.

9. A downhole sampling tool comprising:
a fluid analyzer comprising one or more sensors and configured to measure concentrations of carbon components in a formation fluid sampled from a wellbore extending into a reservoir, wherein the one or more sensors comprise an optical sensor configured to measure an optical density of the formation fluid, obtaining a density of a stock tank oil by performing a simulated flash of the formation fluid from downhole conditions to standard conditions, wherein the standard conditions are about 14.7 psia and 60 degrees Fahrenheit; and
a controller configured to execute instructions stored within the downhole sampling tool to:
determine one or more calibrated parameters based on a previous formation fluid sample obtained from the reservoir, wherein the one or more calibrated parameters comprise a first equilibrium constant for a flashed carbon component of the previous formation fluid sample, the density of the stock tank oil for the simulated flash of the formation fluid, a second equilibrium constant for a first group of $C_3$-$C_5$ carbon components, a third equilibrium constant for a second group of $C_{6+}$ components, or any combination thereof;
determine a ratio of one or more of the carbon components based at least in part on the one or more calibrated parameters, wherein the ratio corresponds to one or more flashed carbon components of the formation fluid; and
calculate a gas-oil ratio based on the concentrations of carbon components obtained via the fluid analyzer and the ratio of the one or more carbon components.

10. The downhole tool of claim 9, wherein the fluid analyzer comprises an optical spectrometer, or a gas chromatograph, or both.

11. The downhole tool of claim 9, comprising an extendable probe to direct the formation fluid into the downhole tool.

12. The downhole tool of claim 9, wherein the controller is configured to execute the instructions to calculate the one or more calibrated parameters based on the previous formation fluid sample.

13. The downhole tool of claim 9, wherein the one or more calibrated parameters comprise the third equilibrium constant for the second group of $C_{6+}$ carbon components.

14. A downhole fluid analysis method comprising:
withdrawing formation fluid, from a wellbore extending into a reservoir comprising the formation fluid, into a sampling system of a downhole sampling tool disposed within the wellbore, wherein the sampling system comprises one or more sensors configured to measure properties of the formation fluid, and wherein the one or more sensors comprises an optical sensor, obtaining a density of a stock tank oil by performing a simulated flash of the formation fluid from downhole conditions to standard conditions, wherein the standard conditions are about 14.7 psia and 60 degrees Fahrenheit; and
analyzing the formation fluid within the downhole tool to the determine the properties of the formation fluid as measured by the one or more sensors of the downhole sampling tool, wherein at least one property of the formation fluid comprises an optical density, and wherein analyzing the formation fluid comprises using a processor configured to:
calculate one or more calibrated parameters based on historical gas-oil ratio data for the reservoir, wherein the one or more calibrated parameters correspond to one or more flashed carbon components of a previous formation fluid sample of the reservoir, and wherein the one or more calibrated parameters comprise a first equilibrium constant for a flashed carbon component of the previous formation fluid sample, the density of the stock tank oil for the simulated flash of the formation fluid, a second equilibrium constant for a first group of $C_3$-$C_5$ carbon components, a third equilibrium constant for a second group of $C_{6+}$ components, or any combination thereof; and
calculate a gas-oil ratio for the formation fluid based on a relationship between the properties of the formation fluid and the one or more flashed carbon components of the previous formation fluid sample.

15. The downhole fluid analysis method of claim 14, wherein analyzing the formation fluid comprises determining concentrations of carbon components within the formation fluid.

16. The downhole fluid analysis method of claim 14, wherein calculating the one or more calibrated parameters comprises determining mixed fluid properties for a third group of carbon components based on the historical gas-oil ratio data.

17. The downhole fluid analysis method of claim 16, wherein the mixed fluid properties comprise an acentric factor, a critical temperature, or a critical pressure, or a combination thereof.

18. The downhole fluid analysis method of claim 14, wherein calculating the one or more calibrated parameters comprises iteratively solving for an amount of flashed gas by adjusting a value of a fourth equilibrium constant based on the historical gas-oil ratio data.

19. The downhole fluid analysis method of claim 14, wherein calculating the gas-oil ratio comprises performing the simulated flash of the formation fluid to standard conditions and determining a ratio of a volume of flashed gas to a volume of the stock tank oil for the simulated flash.

20. The downhole fluid analysis method of claim 14, wherein calculating the one or more calibrated parameters comprises determining, based on the historical gas-oil ratio data, the second equilibrium constant for the first group of $C_3$-$C_5$ carbon components and the third equilibrium constant for the second group of $C_{6+}$ components.

* * * * *